United States Patent [19]

Ferrini

[11] Patent Number: 5,384,319

[45] Date of Patent: Jan. 24, 1995

[54] AMINOALKYLPHENYL COMPOUNDS

[75] Inventor: Pier G. Ferrini, Binningen, Switzerland

[73] Assignee: Ciba-Geigy Corporation, Ardsley, N.Y.

[21] Appl. No.: 170,131

[22] Filed: Dec. 20, 1993

[30] Foreign Application Priority Data

Jan. 6, 1993 [CH] Switzerland .............................. 25/93

[51] Int. Cl.$^6$ .................... A61K 31/495; A61K 31/54; C07D 295/182; C07D 295/192
[52] U.S. Cl. .............................. 514/227.8; 514/235.8; 514/252; 514/255; 514/212; 544/60; 544/121; 544/357; 544/360; 544/372; 544/391; 540/598
[58] Field of Search ................ 544/391, 60, 121, 357, 544/360, 372; 514/252, 255, 227.8, 235.8, 212; 540/598

[56] References Cited

U.S. PATENT DOCUMENTS

| | | | |
|---|---|---|---|
| 3,926,961 | 12/1975 | Ferrini et al. | 544/391 |
| 4,505,913 | 3/1985 | Ferrini et al. | 514/183 |
| 4,804,661 | 2/1989 | Ferrini et al. | 514/255 |
| 5,011,928 | 4/1991 | Venero | 544/373 |
| 5,286,728 | 2/1994 | Ferrini | 514/255 |
| 5,321,027 | 6/1994 | Ferrini et al. | 514/255 |

FOREIGN PATENT DOCUMENTS

| | | |
|---|---|---|
| 250361 | 12/1987 | European Pat. Off. . |
| 0385043 | 9/1990 | European Pat. Off. . |
| 0489690 | 6/1992 | European Pat. Off. . |
| 0524146 | 1/1993 | European Pat. Off. . |
| 2365988 | 3/1977 | Germany . |
| 874096 | 8/1961 | United Kingdom . |
| 2220206 | 1/1990 | United Kingdom . |
| 9000548 | 1/1990 | WIPO . |
| 9109594 | 7/1991 | WIPO . |

OTHER PUBLICATIONS

Kmonicek et al, Collect Czech. Chem. Commun., 55, pp. 1817–1827 (1990).

Derwent Abstract 91-134394/19 corresponding to EP 425,921-A, Published May 8, 1991.
Derwent Abstract 90-290298/38 corresponding to WO 9009-997-A, Published Sep. 7, 1990; filed Feb. 23, 1989.
Chem Abstr. 58, 10211 (1963), Jacob et al.
J. Med Chem 26(1983) 1065–1070; Metz et al "Cloxacepride and Related Compounds . . . ".
J. Med Chem 33 (1990) 2883–91; Lis et al, "Synthesis of (Aryloxy)propanolamines and Related Compounds . . . ".
Chem Abstr. 100, 174, 780c (1984), Agarwal et al.
Derwent Abstr 87-357055/51 corresponding to EP 250,361 (1986).
Chem Abstr. 112, 235261f (1990), Botros et al.
Chem Abstr. 87, 52957 h (1977), Liebenow et al.
Chem Abstr. 56, 10165c (1962), Jacob et al.
Chem Abstr. 57, 15126h (1962), Jacob et al.
Chem Abstr. 58, 3444e (1963), Jacob et al.
Chem Abstr. 58, 4583f (1963), Rhone-Poulec.

Primary Examiner—Emily Bernhardt
Attorney, Agent, or Firm—Irving M. Fishman; Karen G. Kaiser

[57] ABSTRACT

Aminoalkylphenyl derivatives of formula I

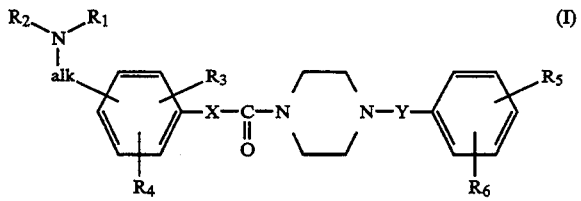

wherein alk, $R_1$–$R_6$, X and Y are as defined in the description, and salts thereof, exhibit properties inhibiting the biosynthesis of interleukin-1 (IL-1) and analgesic properties and can therefore be used as active ingredients in medicaments. They are prepared in a manner known per se.

11 Claims, No Drawings

AMINOALKYLPHENYL COMPOUNDS

The invention relates to novel aminoalkylphenyl derivatives of formula I

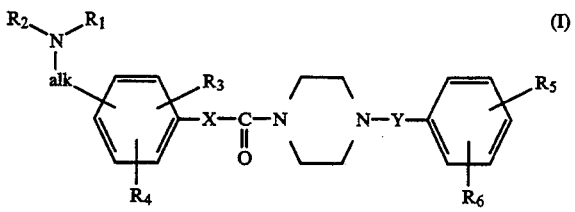

wherein
alk is lower alkylene,
$R_1$ is hydrogen, lower alkyl, lower alkoxy-lower alkyl, lower alkoxy-lower alkoxy-lower alkyl, aryloxy-lower alkyl, aryl-lower alkoxy-lower alkyl, N-lower alkylamino-lower alkyl or N,N-di-lower alkylamino-lower alkyl,
$R_2$ is lower alkenoyl, (carboxy or functionally modified carboxy)-lower alkenoyl, electronegatively substituted lower alkanoyl, carbamoyl, N-lower alkylcarbamoyl, N,N-di-lower alkylcarbamoyl, carboxycarbonyl, lower alkoxycarbonyl-carbonyl, (carbamoyl, N-lower alkylcarbamoyl or N,N-di-lower alkylcarbamoyl)-carbonyl, hydrogen, lower alkyl, lower alkanoyl, carboxy, lower alkoxycarbonyl or aryl-lower alkoxycarbonyl,
$R_3$ and $R_4$ are each independently of the other hydrogen, lower alkyl, halogen, lower alkoxy or lower alkylthio,
$R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino, and
X and Y are each independently of the other a direct bond, lower alkylene or lower alkenylene,
and salts thereof, to processes for the preparation of those compounds, to pharmaceutical compositions comprising those compounds, to the use of those compounds in the therapeutic treatment of the human or animal body or in the preparation of pharmaceutical compositions.

Electronegatively substituted lower alkanoyl is, for example, lower alkanoyl substituted by halogen, amino, lower alkylamino, (carboxy or lower alkoxycarbonyl)-lower alkylamino, di-lower alkylamino; 4- to 6-membered lower alkyleneamino, for example piperidino; morpholino, thiomorpholino, piperazino-unsubstituted or lower alkyl- or lower alkanoyl-substituted in the 4-position-, hydroxy, lower alkoxy, acyloxy, lower alkylthio, lower alkylsulfinyl, lower alkylsulfonyl, arylthio, arylsulfinyl, arylsulfonyl, carboxy, lower alkoxycarbonyl, carbamoyl, N-lower alkylcarbamoyl, N,N-di-lower alkylcarbamoyl or by cyano.

Hereinabove and hereinbelow "lower" radicals and compounds are to be understood as being, for example, those having up to and including 7, preferably up to and including 4, carbon atoms (C atoms).

Lower alkylene is especially $C_1-C_7$alkylene, for example methylene; ethylene, for example 1,2- or 1,1-ethylene; propylene, for example 1,3-, 1,2- or 1,1-propylene; butylene, pentylene, hexylene or heptylene; preferably $C_1-C_4$alkylene and especially methylene or 1,2-ethylene.

Lower alkyl is, for example, $C_1-C_7$alkyl, preferably $C_1-C_4$alkyl, such as especially methyl or secondly ethyl, n-propyl, isopropyl or n-butyl, but may also be, for example, isobutyl, sec-butyl, tert-butyl or a pentyl, hexyl or heptyl group.

Halo-lower alkyl is, for example, trifluoromethyl.

Lower alkenoyl is, for example, $C_3-C_7$alkenoyl, preferably $C_3-C_5$alkenoyl, such as prop-2-enoyl (acryloyl), 2-methylprop-2-enoyl (methacryloyl), but-2-enoyl, but-3-enoyl, 3-methylbut-3-enoyl or pent-4-enoyl.

(Carboxy or functionally modified carboxy)-lower alkenoyl is, for example, lower alkenoyl substituted by carboxy, lower alkoxycarbonyl, carbamoyl, N-lower alkylcarbamoyl, N,N-di-lower alkylcarbamoyl or by cyano, especially by carboxy or by lower alkoxycarbonyl.

Halogen is especially chlorine, fluorine or bromine, but may also be iodine.

Halo-lower alkanoyl is, for example, halo-$C_2-C_7$alkanoyl, halogen being especially chlorine, but secondly also fluorine or bromine, preferably chloro-$C_2-C_4$alkanoyl, such as chloroacetyl, 3-chloropropionyl or 4-chlorobutyryl.

Di-lower alkylamino-lower alkanoyl is, for example, di-$C_1-C_4$alkylamino-$C_2-C_7$alkanoyl, and preferably N,N-dimethylamino-$C_2-C_4$alkanoyl, such as dimethylaminoacetyl.

4- to 6-membered lower alkyleneamino-lower alkanoyl is, for example, pyrrolidino- and preferably piperidino-$C_2-C_4$alkanoyl, for example piperidinoacetyl.

Lower alkoxy-lower alkyl carries the lower alkoxy group preferably in a position higher than the α-position and is, for example, corresponding $C_1-C_4$alkoxy-$C_2-C_4$alkyl, such as 2-methoxyethyl, 2-ethoxyethyl, 2-propoxyethyl, 2-isopropoxyethyl, 3-methoxypropyl, 3-ethoxypropyl, 3-isopropoxypropyl or 4-methoxybutyl.

Carboxycarbonyl is the group —C(=O)—COOH.

Aryl is, for example, phenyl that is unsubstituted or is substituted by one or two substituents selected from the group consisting of lower alkyl, lower alkoxy, hydroxy, halogen and trifluoromethyl, and is especially phenyl.

Acyl is, for example, lower alkanoyl.

Salts of compounds of formula I are especially pharmaceutically acceptable salts, for example acid addition salts with suitable mineral acids, such as hydrohalic acids, sulfuric acid or phosphoric acid, for example hydrochlorides, hydrobromides, sulfates, hydrogen sulfates or phosphates, salts with suitable aliphatic or aromatic sulfonic acids or N-substituted sulfamic acids, for example methanesulfonates, benzenesulfonates, p-toluenesulfonates or N-cyclohexylsulfamates (cyclamates), or salts with strong organic carboxylic acids, such as lower alkanecarboxylic acids or saturated or unsaturated or hydroxylated aliphatic dicarboxylic acids, for example acetates, oxalates, malonates, maleinates, fumarates, maleates, tartrates or citronates.

For the purposes of isolation or purification it is also possible to use pharmaceutically unacceptable salts. Only the pharmaceutically acceptable, non-toxic salts are used therapeutically and these are therefore preferred.

The compounds of formula I and the pharmaceutically acceptable salts thereof exhibit valuable pharmacological properties. They exhibit, especially, marked inhibitory action on the biosynthesis of interleukin-1 (IL-1). IL-1 belongs to the class of proinflammatory proteins and plays an essential role, for example, in the synthesis of prostaglandins, in the synthesis of neutral proteases by fibroblasts, synovial cells and chondrocytes, in the activation of endothelial cells and in the induction of other proinflammatory cytokines, such as the α-tumour necrosis factor (TNF) and interleukin-6 (IL-6). It also stimulates bone resorption, regulates the body temperature of warm-blooded animals and regulates inter alia the development, activation, differentiation and proliferation of lymphocytes. From the therapeutic standpoint, special importance is attached to the inhibitory action of compounds of formula I and the pharmaceutically acceptable salts thereof on the biosynthesis of IL-1, TNF and IL-6. This can be demonstrated in vitro, for example, by lipo-polysaccharide-stimulated (LPS-stimulated) human monocytes in accordance with C. Rordorf-Adam et al., Drugs Exptl. Clin. Res. XV, 355-362 (1989) in a concentration range from approximately 0.1 μM and in vivo in mice by reference to the inhibition of the LPS-induced formation of serum amyloid P (SAP) at an $ED_{50}$ of approximately from 1 to 15 mg/kg p.o. and in rats by reference to the lowering of LPS-induced artificial fever at an $ED_{50}$ of approximately from 0.05 to 3.5 mg/kg p.o.

As a result of those properties, the compounds of formula I and the pharmaceutically acceptable salts thereof are excellently suitable for the therapeutic treatment of diseases in which an overproduction of IL-1 plays a causative or aggravating role, such as inflammatory and degenerative diseases of the joints, for example rheumatoid arthritis, osteoarthrosis, psoriatic or infectious arthritis, Reiter's syndrome, gout and traumatic arthritis, and other acute or chronic inflammations, for example inflammatory intestinal diseases, meningitis, skin diseases, for example psoriasis or Pemphigus vulgaris, allergic skin reactions, atherosclerosis and autoimmune diseases, such as diabetes (type 1) and thyroiditis.

Examples of other diseases in which an overproduction of IL-1 plays a causative or aggravating role are, for example: bone metabolism regulation disorders, for example Paget's disease, osteoporosis, periodontitis or malignancies; or endotoxic shock, for example associated with fever, hypotension and fulminant liver failure.

The compounds of formula I and the pharmaceutically acceptable salts thereof also have a marked analgesic action which can be demonstrated, for example, by reference to the inhibition of the phenyl-p-benzoquinone-induced writhing syndrome in mice, for example in an experimental procedure based on Hendershot and Forsaith, J. Pharmacol. Exp. Therap. 125, 237 (1959), at an $ED_{50}$ of approximately from 1 to 30 mg/kg p.o.

Accordingly, the compounds of formula I and the pharmaceutically acceptable salts thereof can also be used as active ingredients in analgesic medicaments for the treatment of painful conditions of different origins, especially as peripheral analgesics.

The invention relates preferably to the compounds of formula I wherein alk is lower alkylene, $R_1$ is hydrogen, lower alkyl, lower alkoxy-lower alkyl, lower alkoxy-lower alkoxy-lower alkyl; phenoxy-lower alkyl or phenyl-lower alkoxy-lower alkyl, the phenyl group in each of the two last-mentioned radicals being unsubstituted or substituted by lower alkyl, trifluoromethyl, lower alkoxy, halogen and/or by hydroxy; N-lower alkylamino-lower alkyl or N,N-di-lower alkylamino-lower alkyl, $R_2$ is lower alkenoyl, (carboxy, lower alkoxycarbonyl, carbamoyl, N-lower alkylcarbamoyl, N,N-di-lower alkylcarbamoyl or cyano)-lower alkenoyl, halo-lower alkanoyl, amino-lower alkanoyl, N-lower alkylamino-lower alkanoyl, N-[(carboxy or lower alkoxycarbonyl)-lower alkylamino]-lower alkanoyl, N,N-di-lower alkylamino-lower alkanoyl, $C_4$–$C_6$lower alkyleneamino-lower alkanoyl, morpholino-lower alkanoyl, thiomorpholino-lower alkanoyl; piperazino-lower alkanoyl wherein the piperazino radical is unsubstituted or substituted in the 4-position by lower alkyl or by lower alkanoyl; hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkylsulfonyl-lower alkanoyl; phenylthio-lower alkanoyl, phenylsulfinyl-lower alkanoyl or phenylsulfonyl-lower alkanoyl, the phenyl group in each of the three last-mentioned radicals being unsubstituted or substituted by lower alkyl, lower alkoxy, halogen and/or by hydroxy; carboxy-lower alkanoyl, lower alkoxycarbonyl-lower alkanoyl, carbamoyl-lower alkanoyl, N-lower alkylcarbamoyl-lower alkanoyl, N,N-di-lower alkylcarbamoyl-lower alkanoyl, cyano-lower alkanoyl, carbamoyl, N-lower alkylcarbamoyl, N,N-di-lower alkylcarbamoyl, carboxycarbonyl, lower alkoxycarbonyl-carbonyl, (carbamoyl, N-lower alkylcarbamoyl or N,N-di-lower alkylcarbamoyl)-carbonyl, hydrogen, lower alkanoyl, carboxy, lower alkoxycarbonyl or phenyl-lower alkoxycarbonyl wherein the phenyl group is unsubstituted or substituted by lower alkyl, lower alkoxy, halogen and/or by hydroxy, $R_3$ and $R_4$ are each independently of the other hydrogen, lower alkyl, halogen, lower alkoxy or lower alkylthio, $R_5$ and $R_6$ are each independently of the other hydrogen, lower alkyl, halo-lower alkyl, lower alkoxy, lower alkylthio, halogen, amino, lower alkylamino, di-lower alkylamino or lower alkanoylamino, and X and Y are each independently of the other a direct bond, lower alkylene or lower alkenylene, and salts thereof.

The invention relates especially preferably to the compounds of formula I wherein alk is lower alkylene, $R_1$ is hydrogen, lower alkyl, lower alkoxy-lower alkyl, lower alkoxy-lower alkoxy-lower alkyl, phenoxy-lower alkyl, N-lower alkylamino-lower alkyl or N,N-di-lower alkylamino-lower alkyl, $R_2$ is lower alkenoyl, (carboxy or lower alkoxycarbonyl)-lower alkenoyl, halo-lower alkanoyl, N-lower alkylamino-lower alkanoyl, N-[(carboxy or lower alkoxycarbonyl)-lower alkylamino]-lower alkanoyl, N,N-di-lower alkylamino-lower alkanoyl, piperidino-lower alkanoyl, hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkylsulfonyl-lower alkanoyl, phenylthio-lower alkanoyl, phenylsulfinyl-lower alkanoyl, phenylsulfonyl-lower alkanoyl, carboxy-lower alkanoyl, lower alkoxycarbonyl-lower alkanoyl, hydrogen or lower alkanoyl, $R_3$ and $R_4$ are each independently of the other hydrogen, lower alkyl, halogen, lower alkoxy or lower alkylthio, $R_5$ and $R_6$ are each independently of the other hydrogen, lower alkyl, trifluoromethyl, lower alkoxy, lower alkylthio, halogen or di-lower alkylamino, and X and Y are each independently of the other a direct bond, lower alkylene or lower alkenylene, and salts thereof.

The invention relates very especially preferably to the compounds of formula I wherein
  alk is methylene or 1,2-ethylene,
  $R_1$ is hydrogen, lower alkyl or lower alkoxy-lower alkyl,
  $R_2$ is lower alkenoyl, (carboxy or lower alkoxycarbonyl)-lower alkenoyl or halo-lower alkanoyl, or, when $R_1$ is lower alkoxy-lower alkyl, $R_2$ may also be hydrogen,
  $R_3$ and $R_4$ are each independently of the other hydrogen, lower alkyl, halogen, lower alkoxy or lower alkylthio,
  $R_5$ is lower alkylthio, chlorine, fluorine or bromine,
  $R_6$ is hydrogen,
  X is a direct bond or 1,2-ethenylene, and
  Y is 1,2-ethylene,
and pharmaceutically acceptable salts thereof.

The invention relates especially also to the compounds of formula Ia

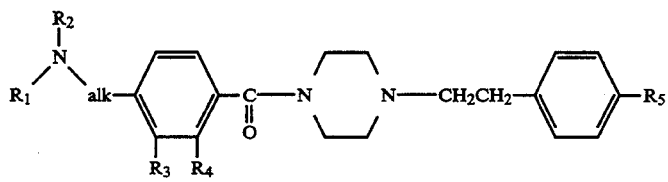

wherein
  alk is lower alkylene,
  $R_1$ is hydrogen, lower alkyl or lower alkoxy-lower alkyl,
  $R_2$ is lower alkenoyl, (carboxy or lower alkoxycarbonyl)-lower alkenoyl, or lower alkanoyl substituted by halogen, di-lower alkylamino, 4- to 6- membered lower alkyleneamino or by lower alkylthio, or, when $R_1$ is lower alkoxy-lower alkyl, $R_2$ may also be hydrogen,
  $R_3$ and $R_4$ are each independently of the other hydrogen, lower alkyl, chlorine, fluorine or bromine, and
  $R_5$ is lower alkylthio, chlorine, fluorine or bromine,
and salts thereof.

The invention relates especially to compounds of formula Ia wherein
  alk is $C_1$–$C_4$alkylene,
  $R_1$ is hydrogen, $C_1$–$C_4$alkyl or $C_1$–$C_4$alkoxy-$C_2$–$C_4$alkyl,
  $R_2$ is $C_3$–$C_7$alkenoyl, (carboxy or $C_1$–$C_4$alkoxycarbonyl)-$C_3$–$C_7$alkenoyl chloro $C_2$–$C_4$alkanoyl, $C_1$–$C_4$alkylthio-, $C_1$–$C_4$alkylsulfinyl- or $C_1$–$C_4$alkylsulfonyl-$C_2$–$C_4$-alkanoyl, or, when $R_1$ is $C_1$–$C_4$alkoxy-$C_2$–$C_4$alkyl, $R_2$ may also be hydrogen,
  $R_3$ and $R_4$ are each independently of the other hydrogen, $C_1$–$C_4$alkyl, fluorine or chlorine, and
  $R_5$ is chlorine or bromine,
and pharmaceutically acceptable salts thereof.

The invention relates especially to compounds of formula Ia wherein
  alk is methylene or 1,2-ethylene,
  $R_1$ is hydrogen, methyl, ethyl or 2-isopropoxyethyl,
  $R_2$ is prop-2-enoyl, 3-(carboxy or $C_1$–$C_4$alkoxycarbonyl)-prop-2-enoyl, chloroacetyl, 3-chloropropionyl, methylthioacetyl or ethylthioacetyl,
  $R_3$ and $R_4$ are each independently of the other hydrogen, methyl, fluorine or chlorine, and
  $R_5$ is chlorine or bromine,
and pharmaceutically acceptable salts thereof.

The invention relates more especially to compounds of formula Ia wherein
  alk is methylene or 1,2-ethylene,
  $R_1$ is hydrogen or 2-isopropoxyethyl,
  $R_2$ is chloroacetyl,
  $R_3$ and $R_4$ are each independently of the other hydrogen, methyl, fluorine or chlorine, and
  $R_5$ is chlorine or bromine,
and pharmaceutically acceptable salts thereof.

The invention relates specifically to the compounds of formula I mentioned in the Examples and the salts thereof, especially the pharmaceutically acceptable salts thereof.

The process for the preparation of compounds of formula I is based on methods known per se and is carried out, for example, as follows:

a) a compound of formula II

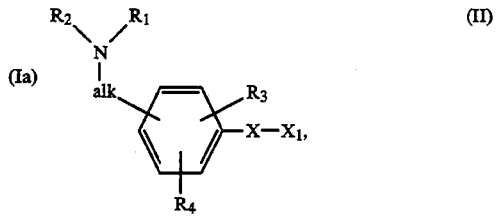

wherein $X_1$ is carboxy or reactive functionally modified carboxy, or a salt thereof, is reacted with a compound of formula III

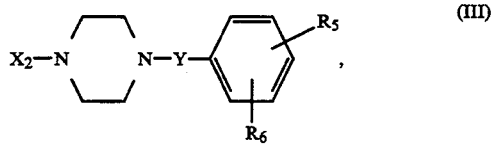

wherein $X_2$ is hydrogen or an amino-protecting group, or b) a compound of formula IV

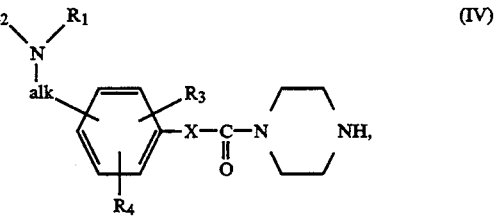

or a salt thereof, is reacted with a compound of formula V

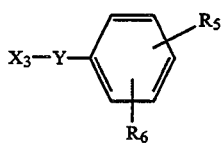

wherein $X_3$ is hydroxy or reactive esterified hydroxy, or c) a compound of formula VI

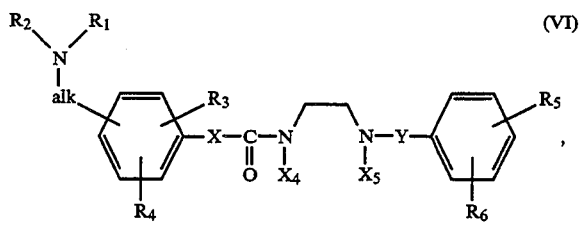

wherein one of the radicals $X_4$ and $X_5$ is hydrogen and the other is a group of the formula $-CH_2-CH_2-X_3$ (VIa) and $X_3$ is hydroxy or reactive esterified hydroxy, is cyclised, or d) a compound of formula VII

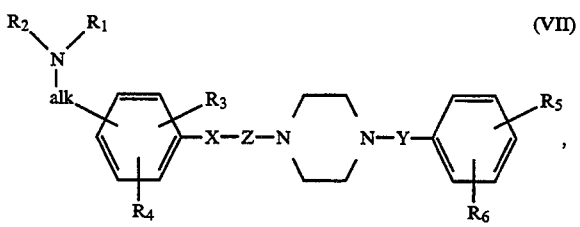

wherein Z is a group that can be oxidised to carbonyl, is oxidised, or e) the radical $R_2$ is introduced ($R_2 \neq H$) into a compound of formula VIII

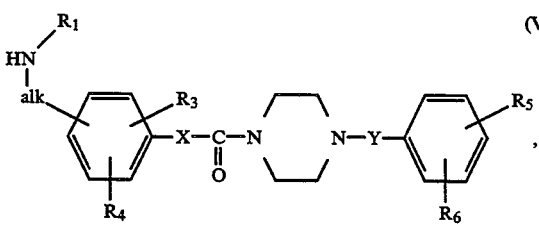

or f) for the preparation of compounds wherein $R_1$ is lower alkoxy-lower alkyl, the radical $R_1$ is introduced into a compound of formula IX

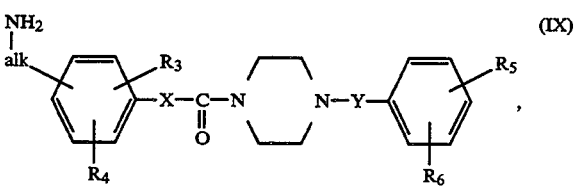

or g) an amine of formula X

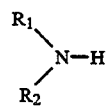

is reacted with a compound of formula XI

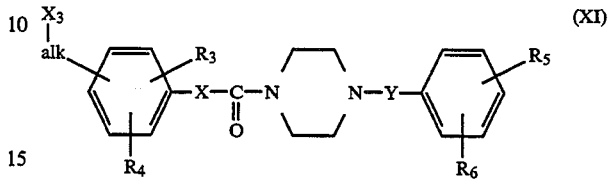

wherein $X_3$ is hydroxy or reactive esterified hydroxy; and, if desired, a compound of formula I obtainable in accordance with any one of the above processes or by another method is converted into a different compound of formula I, a mixture of isomers obtainable in accordance with the process is separated into its components, a free compound of formula I obtainable in accordance with the process is converted into a salt and/or a salt obtainable in accordance with the process is converted into the free compound of formula I or into a different salt.

The reactions described hereinabove and hereinbelow are carried out in a manner known per se, for example in the absence or, usually, in the presence of a suitable solvent or diluent or a mixture thereof, the operation being carried out, as required, with cooling, at room temperature or with heating, for example in a temperature range of from approximately −78° to the boiling temperature of the reaction medium, preferably from approximately −10° to approximately 150° C., and, if necessary, in a closed vessel, under pressure, in an inert gas atmosphere and/or under anhydrous conditions.

In the starting materials the basic centre can be, for example, in the form of an acid addition salt, for example with an acid listed above in connection with salts of compounds of formula I, while starting compounds of formula II wherein $X_1$ is carboxy can form salts with bases. Suitable salts with bases are, for example, corresponding alkali meted or alkaline earth metal salts, for example sodium, potassium or magnesium salts, pharmaceutically acceptable transition metal salts, such as zinc or copper salts, or salts with ammonia or organic amines, such as cyclic amines, such as mono-, di- or tri-hydroxy-$C_1$-$C_7$alkylamines, hydroxy-$C_1$-$C_7$alkyl-$C_1$-$C_7$alkylamines or polyhydroxy-$C_4$-$C_7$alkylamines. Cyclic amines are, for example, morpholine, thiomorpholine, piperidine or pyrrolidine. There come into consideration as mono-$C_1$-$C_7$alkylamines, for example, ethylamine or tert-butylamine; as di-$C_1$-$C_7$alkylamines, for example, diethylamine or diisopropylamine; and as tri-$C_1$-$C_7$alkylamines, for example, trimethylamine or triethylamine. Corresponding hydroxy-$C_1$-$C_7$alkylamines are, for example, mono-, di- or triethanolamines, and hydroxy-$C_1$-$C_7$alkyl-$C_1$-$C_7$alkylamines are, for example, N,N-dimethylamino-or N,N-diethylaminoethanol, and also glucosamine as a polyhydroxy-$C_6$alkylamine.

Reactive functionally modified carboxy $X_1$ is, for example, esterified carboxy, especially reactive esterified carboxy, anhydridised carboxy or amidated carboxy.

Esterified carboxy is, for example, unsubstituted or substituted $C_1$–$C_7$alkoxycarbonyl, such as ethoxycarbonyl, but preferably reactive esterified carboxy, for example vinyloxycarbonyl, which may be additionally activated, for example, by $C_1$–$C_7$alkoxy or by unsubstituted or substituted carbamoyl, such as 1-$C_1$–$C_7$alkoxy-, for example 1-ethoxyvinyloxycarbonyl, or 2-(N-$C_1$-$C_7$alkylcarbamoyl)-, for example 2-(N-ethylcarbamoyl)-vinyloxycarbonyl, and also phenoxy- or thiophenoxy-carbonyl that is unsubstituted or substituted, for example, by nitro, halogen, $C_1$–$C_7$alkanesulfonyl or by phenylazo, such as 4-nitro-, 2,4,5-trichloro-, pentachloro-, 4-methanesulfonyl-, 4-phenylazo-phenoxycarbonyl, thiophenoxy- or 4-nitrothiophenoxy-carbonyl, and also activated methoxycarbonyl, for example methoxycarbonyl substituted by cyano or by free or esterified carboxy, especially cyanomethoxycarbonyl. Reactive esterified carboxy can also be 1,1- or 1,3-disubstituted 2-isoureidocarbonyl, such as 1,1-di-lower alkyl-, 1,1-diaryl- or 1,1-diaryl-$C_1$–$C_7$alkyl-2-isoureidocarbonyl, for example 1,1-diethyl-, 1,1-diphenyl- or 1,1-dibenzyl-2-isoureidocarbonyl, or 1,3-dicycloalkyl-, for example 1,3-dicyclohexyl-2-isoureidocarbonyl, or N-$C_2$–$C_7$alkyleneamino-oxycarbonyl, such as N-piperidinyl-oxycarbonyl, and also N-imido-oxycarbonyl, for example N-succinimido-oxy- or N-phthalimido-oxy-carbonyl.

Anhydridised carboxy is to be understood as being, for example, unbranched or branched $C_1$–$C_7$alkoxycarbonyloxycarbonyl, such as ethoxy- or isobutoxy-carbonyloxycarbonyl, halocarbonyl, such as chlorocarbonyl, azidocarbonyl, halophosphoryloxycarbonyl, such as dichlorophosphoryloxycarbonyl, or unsubstituted or substituted, for example halo- or aryl-substituted, $C_1$-$C_7$alkanoyloxycarbonyl, such as pivaloyloxy-, trifluoroacetoxy- or phenylacetoxy-carbonyl.

Reactive amidated carboxy is, for example, unsubstituted or substituted, for example $C_1$–$C_7$alkyl-substituted, 1-imidazolyl- or 1-pyrazolyl-carbonyl, such as 3,5-dimethylpyrazolycarbonyl.

An amino-protecting group $X_2$ is, for example, acyl, such as $C_1$–$C_7$alkanoyl, for example formyl or acetyl, halocarbonyl, such as chlorocarbonyl, and also unsubstituted or substituted aryl- or heteroaryl-sulfonyl, such as 2-pyridyl- or 2-nitrophenyl-sulfonyl.

In the context of the description of the process hereinabove and hereinbelow, unless otherwise defined, reactive esterified hydroxy, for example $X_3$, is especially hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, unsubstituted or substituted, for example halo-substituted, $C_1$–$C_7$alkanesulfonyloxy, for example methane- or trifluoromethane-sulfonyloxy, $C_3$–$C_7$cycloalkanesulfonyloxy, for example cyclohexanesulfonyloxy, or unsubstituted or substituted, for example $C_1$–$C_7$alkyl- or halo-substituted, benzenesulfonyloxy, for example p-bromophenyl- or p-toluene-sulfonyloxy.

Where, for example, bases are used in the reactions described hereinabove and hereinbelow, unless specified to the contrary, the following bases come into consideration, for example: alkali metal hydroxides, hydrides, amides, alkanolates, carbonates, triphenylmethylides, di-$C_1$–$C_7$-alkylamides, amino-$C_1$–$C_7$alkylamides or $C_1$–$C_7$alkylsilylamides, or naphthylamines, $C_1$-$C_7$alkylamines, basic heterocycles, ammonium hydroxides, and also carbocyclic amines. There may be mentioned by way of example: lithium hydroxide, sodium hydroxide, hydride, amide or ethanolate, potassium tert-butanolate or carbonate, lithium triphenylmethylide or diisopropylamide, potassium 3-(aminopropyl)amide or bis(trimethylsilyl)amide, dimethylaminonaphthalene, di- or tri-ethylamine, pyridine, benzyltrimethylammonium hydroxide, 1,5-diazabicyclo[4.3.0]non-5-ene (DBN) and also 1,8-diazabicyclo[5.4.0]undec-7-ene (DBU).

Variant a);.

The N-acylation in accordance with the process is carried out in a manner known per se, if necessary in the presence of a condensation agent, especially a basic condensation agent. Suitable bases are, for example, representatives of the bases listed above. Frequently the basicity of the compound of formula III is also sufficient.

When $X_1$ is carboxy there are formed, for example, primarily the corresponding ammonium salts which can be dehydrated by heating or by treatment with suitable dehydrating agents (as condensation agents), such as carbodiimides, for example N,N'-di-lower-alkyl-or N,N'-dicycloalkyl-carbodiimide, such as N,N'-diethyl-, N,N'-diisopropyl-or N,N'-dicyclohexyl-carbodiimide, advantageously with the addition of N-hydroxysuccinimide or unsubstituted or substituted, for example halo-, lower alkoxy- or lower alkyl-substituted, 1-hydroxybenzotriazole or N-hydroxy-5-norbornene-2,3-dicarboxamide, and also N,N-carbonyldiimidazole. With carbodiimides it is possible to form intermediately, for example, also the corresponding 1-isoureidocarbonyl compounds. As water-binding condensation agents there may also be used N-ethoxycarbonyl-2-ethoxy-1,2-dihydroquinoline, phosphorylcyanamides or phosphorylazides, such as diethylphosphorylcyanamide or diphenylphosphorylazide, triphenylphosphine disulfide or 1-lower alkyl-2-halopiperidinium halides, such as 1-methyl-2-chloropyridinium iodide.

Some of the starting materials used in this process variant are known or they can be prepared according to processes known per se.

For the preparation of compounds of formula II wherein $X_1$ is unsubstituted or substituted $C_1$–$C_7$alkoxycarbonyl it is usually possible to use as starting material the free acid ($X_1$=carboxy) or an acid anhydride ($X_1$ is, for example, halocarbonyl), which is reacted, for example, with the corresponding alcohol, which is if necessary in reactive form, for example a $C_1$–$C_7$alkyl halide. The preparation of compounds of formula II wherein $X_1$ is vinyloxycarbonyl, which may be additionally activated, can be carried out, for example, by transesterification of a $C_1$–$C_7$alkyl ester with vinyl acetate (activated vinyl ester method), by reaction of the free acid of compounds of formula II with lower alkoxyacetylene (for example ethoxyacetylene method) or, analogously to the Woodward method, with a 1,2-oxazolium salt. Compounds of formula II containing unsubstituted or substituted phenoxy- or thiophenoxy-carbonyl can be obtained, for example, starting from the free acid in accordance with the carbodiimide method by reaction with the corresponding (thio)phenol. Likewise starting from the free acid of formula II it is possible to obtain compounds of formula II wherein $X_1$ is activated methoxycarbonyl or 1,1- or 1,3-disubstituted 2-isoureidocarbonyl, for example by reaction with a haloacetonitrile, for example chloroacetonitrile, (cyanomethyl ester method) or with a carbodiimide or cyanamide (carbodiimide or cyanamide method), respectively.

The preparation of N-$C_2$-$C_7$alkyleneamino-oxycarbonyl or N-imido-oxycarbonyl compounds of formula II can be carried out, for example, using the free acid of formula II from corresponding N-hydroxy compounds with the aid of carbodiimides in accordance with the activated N-hydroxy esters method. For the preparation of compounds of formula II wherein $X_1$ is unbranched or branched $C_1$-$C_7$alkoxycarbonyloxycarbonyl, halophosphoryloxycarbonyl or unsubstituted or substituted $C_1$-$C_7$alkanoyloxycarbonyl, there can be used as starting material, for example, the free acid of formula II which can be treated, for example, with a corresponding halide, such as an unsubstituted or substituted $C_1$-$C_7$alkylcarbonic acid halide (mixed O-carbonic acid anhydrides method), phosphorus oxyhalide (for example phosphorus oxychloride method) or an unsubstituted or substituted $C_1$-$C_7$alkanoyl halide (mixed carboxylic acid halides method). Azidocarbonyl compounds of formula II can be obtained, for example, by treatment of corresponding hydrazides with nitrous acid (azide method). For the preparation of compounds of formula II wherein $X_1$ is unsubstituted or substituted 1-imidazolylcarbonyl or 1-pyrazolylcarbonyl, the free acid of formula II is reacted, for example, with di(1-imidazolyl)carbonyl (imidazolide method) or the relevant hydrazide, for example with a corresponding 1,3-diketone (pyrazolide method), respectively.

Variant b):

The radical $X_3$ is especially reactive esterified hydroxy, for example halogen, such as chlorine.

The N-alkylation in accordance with the process is carried out in a manner known per se, if necessary in the presence of a base, for example one of the bases mentioned above.

Some of the starting materials used in this process variant are known or they can be prepared in a manner known per se.

For example, the starting material of formula IV can be prepared by reacting a compound of formula II, or a salt thereof, wherein $X_1$ is carboxy or reactive functionally modified carboxy with a compound of formula IVa

(IVa)

or a salt thereof, wherein $Z_1$ is hydrogen or an amino-protecting group, such as benzyl, in the manner described in variant a) and, where appropriate, removing the amino-protecting group, for example benzyl, by customary hydrogenolysis.

Variant c):

The cyclisation (intramolecular N-alkylation) in accordance with the process is carried out in a manner known per se, if necessary in the presence of a condensation agent, especially a basic condensation agent. The bases used are, for example, those mentioned above.

$X_3$ is in this case especially reactive esterifed hydroxy, preferably halogen, such as chlorine.

The starting material can be prepared in a manner known per se, for example starting from a compound of formula II, or a salt thereof, wherein $X_1$ is carboxy or reactive functionally modified carboxy, which compound is first reacted with a compound of formula

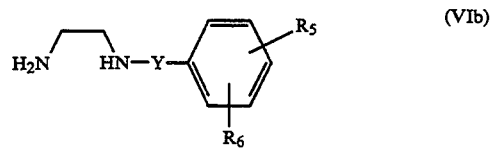

(VIb)

analogously to variant a). In the next reaction step the resulting compound is reacted with a compound of the formula $X_3$—$CH_2$—$CH_2$—$X_3$ (VIc) under N-alkylating conditions in accordance with variant b).

Variant d):

A group Z that can be oxidised to —CO— is especially —$CH_2$—. The oxidation of corresponding compounds of formula VII is effected with the aid of a suitable oxidising agent, there preferably being used tetra-$C_1$-$C_4$alkylammonium permanganates that are unsubstituted or substituted, for example by a phenyl radical, especially benzyltriethylammonium permanganate.

The starting material of formula VII is prepared in a manner known per se, for example starting from a compound of formula III wherein $X_2$ is hydrogen, which compound is reacted under the N-alkylating conditions described in variant b) with a compound of formula VIIa

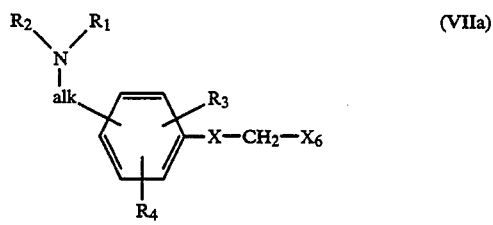

(VIIa)

wherein $X_6$ is hydroxy or especially reactive esterified hydroxy, especially halogen, such as chlorine or bromine.

Variant e):

The introduction of lower alkenoyl or electronegatively substituted lower alkanoyl (N-acylation) is carried out in customary manner, if necessary in the presence of a condensation agent, especially a basic condensation agent. Suitable bases are, for example, representatives of the bases mentioned above.

Variant f):

The introduction of lower alkoxy-lower alkyl $R_1$ (N-alkoxyalkylation) is effected in customary manner, if necessary in the presence of a condensation agent, especially a basic condensation agent. Suitable bases are, for example, representatives of the bases mentioned above.

Variant g):

Variant g) is the N-alkylation, known per se, of ammonia or primary or secondary amines. It also includes all variants that allow the selective synthesis of primary, secondary and tertiary amines by this method. Reactive esterified hydroxy $X_3$ is in this case, for example, halogen, such as chlorine.

A compound according to the invention obtainable in accordance with the process can be converted into a different compound according to the invention in a manner known per se.

In compounds according to the invention wherein $R_1$ is lower alkoxy-lower alkyl and $R_2$ is hydrogen, the amino group can be N-acylated in the manner indicated above under variant a), b) or e). Likewise, a compound of formula I wherein $R_1$ is hydrogen and $R_2$ is lower alkenoyl or electronegatively substituted lower alkanoyl can be N-substituted by lower alkoxy-lower alkyl or N-lower alkylated in accordance with the manner described in process variant f). The N-lower alkylation can also be carried out by reduction analogously to the Leuckart-Wallach (or Eschweiler-Clarke) reaction using carbonyl compounds, for example using formic acid as reducing agent.

Resulting salts can be converted into the free compounds in a manner known per se, for example by treatment with a base, such as an alkali metal hydroxide, a metal carbonate or hydrogen carbonate, or ammonia, or with another salt-forming base mentioned at the beginning, or with an acid, such as a mineral acid, for example hydrochloric acid, or with another salt-forming acid mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing the free acid and converting it into a salt again.

The compounds of formula I, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

The invention relates also to those forms of the process according to which a compound obtainable as intermediate at any stage of the process is used as starting material and the remaining steps are carried out or a starting material is used in the form of a salt or especially is formed under the reaction conditions.

The invention relates also to the novel starting materials, which have been developed specifically for the preparation of the compounds according to the invention, especially the group of starting materials that result in the compounds of formula I described at the beginning as being preferred, to processes for the preparation thereof and to the use thereof as intermediates.

The novel compounds of formula I can be used, for example, in the form of pharmaceutical compositions comprising a therapeutically effective amount of the active ingredient, optionally together with inorganic or organic, solid or liquid, pharmaceutically acceptable carriers that are suitable for enteral, for example oral, or parenteral administration. For example, there are used tablets or gelatin capsules comprising the active ingredient together with diluents, for example lactose, dextrose, saccharose, mannitol, sorbitol, cellulose and/or lubricants, for example silica, talc, stearic acid or salts thereof, such as magnesium or calcium stearate, and/or polyethylene glycol. Tablets may also comprise binders, for example magnesium aluminium silicate, starches, such as corn, wheat, rice or arrowroot starch, gelatin, tragacanth, methylcellulose, sodium carboxymethylcellulose and/or polyvinylpyrrolidone, and, if desired, disintegrators, for example starches, agar, alginic acid or a salt thereof, for example sodium alginate, and/or effervescent mixtures, or absorbents, colourings, flavourings and sweeteners. The novel compounds of formula I can also be used, for example, in the form of parenterally administrable compositions or in the form of infusion solutions. Such solutions are preferably isotonic aqueous solutions or suspensions, it being possible, for example in the case of lyophilised compositions that comprise the active ingredient on its own or together with a carrier, for example mannitol, for such solutions or suspensions to be made up before use. The pharmaceutical compositions may be sterilised and/or comprise excipients, for example preservatives, stabilisers, wetting agents and/or emulsifiers, solubilisers, salts for regulating the osmotic pressure and/or buffers. The present pharmaceutical compositions which, if desired, may comprise further pharmacologically active ingredients, are prepared in a manner known per se, for example by means of conventional mixing, granulating, confectioning, dissolving or lyophilising processes, and comprise approximately from 0.1% to 100%, especially from approximately 1% to approximately 50%, and in the case of lyophilisates up to 100%, active ingredient.

The invention relates also to the use of the compounds of formula I, preferably in the form of pharmaceutical compositions. The dose may depend on various factors, such as mode of administration, species, age and/or individual condition. The daily doses to be administered in the case of oral administration are from approximately 0.25 to approximately 10 mg/kg and for warm-blooded animals of approximately 70 kg body weight preferably from approximately 20 mg to approximately 500 mg.

The following Examples serve to illustrate the invention; temperatures are given in degrees Celsius, pressures in mbar. The following abbreviations are used: ether=diethyl ether, DMF=dimethylformamide, $(BOC)_2O$=di-tert-butyl dicarbonate.

EXAMPLE 1

1-{4-[N-(2-isopropoxyethyl)-N-chloroacetylaminomethyl]-benzoyl}-4-[2-(4-chlorophenyl)-ethyl]-piperazine hydrochloride 1.43 g of 1-[2-(4-chlorophenyl)-ethyl]-piperazine are dissolved with 0.83 g of N-ethyldiisopropylamine (Hünig base) in 35 ml of methylene chloride. 2 g of crude 4-[N-(2-isopropoxymethyl)-N-chloroacetylaminomethyl]-benzoic acid chloride in approximately 10 ml of methylene chloride are added dropwise thereto. The clear solution so obtained is stirred overnight at room temperature, then washed with water, dried over sodium sulfate and concentrated to dryness by evaporation. The crude oil (3.2 g) is chromatographed on silica gel (eluants: methylene chloride/acetone 500:150 and methylene chloride/acetone/methanol 500:100:25) and crystallised from ethanol/ether in the form of the hydrochloride. The title compound having a melting point of 186°–188° is obtained.

The starting material is prepared as follows:

(a) 30 g of 4-aminomethylbenzoic acid (Janssen) are suspended in 250 ml of acetic anhydride and 250 ml of pyridine and stirred at an external temperature of 60°, the 4-aminomethylbenzoic acid entering into solution after about 45 minutes. After 2 hours the heating is removed and the solution is stirred at room temperature overnight. The solution is concentrated by evaporation. 400 ml of water are added to the crystalline material; the resulting suspension is acidified with 2N hydrochloric acid, stirred vigorously for 30 minutes and filtered with suction. The colourless crystals are subsequently washed with water and then dissolved in 250 ml of ethanol. The solution is dried over sodium sulfate and diluted with 200 ml of ether. On cooling, the 4-acetylaminomethylbenzoic acid having a melting point of 196°–200° crystallises.

(b) 2.5 g of 4-acetylaminomethylbenzoic acid are dissolved warm in 20 ml of absolute ethanol. 0.3 ml of concentrated sulfuric acid is added thereto and the mixture is boiled at reflux for 10 hours. The solution is concentrated to dryness by evaporation. The residue is dissolved in ethyl acetate and washed with sodium carbonate solution and water, dried and concentrated by evaporation. The 4-acetylaminomethylbenzoic acid ethyl ester, recrystallised from ethyl acetate/petroleum ether, melts at 100°–101°.

(c) 6.6 g of the ester obtained according to (b) are dissolved in 60 ml of acetonitrile, and 0.36 g of 4-dimethylaminopyridine are added. 8 g of $(BOC)_2O$ in 10 ml of acetonitrile are added dropwise thereto in the course of 5 minutes. The mixture is left to stand overnight at room temperature, yielding 4-(N-acetyl-N-tert-butoxycarbonylaminomethyl)-benzoic acid ethyl ester in solution. 5.9 g of 2-diethylaminoethylamine are added to that solution and the mixture is left to stand for 5 hours. The further steps of the operation are as follows: the mixture is concentrated by evaporation, the residue is taken up in ethyl acetate, washed with sodium chloride solution and water, again concentrated by evaporation, chromatographed on silica gel (eluants: methylene chloride and methylene chloride/acetone 4:1) and recrystallised from ether/petroleum ether, yielding the 4-tert-butoxycarbonylaminomethylbenzoic acid ethyl ester, melting point 96°–97°.

(d) 5.9 g of 4-tert-butoxycarbonylaminomethylbenzoic acid ethyl ester are dissolved in 50 ml of DMF. 1.5 g of pulverulent KOH are added. The mixture is stirred for 15 minutes at 55° and 5.5 g of O-(2-isopropoxyethyl)-tosylate are added. The mixture is stirred for 5 hours at 60°–65°. The solution is concentrated by evaporation, yielding the oily 4-[N-(2-isopropoxyethyl)-N-tert-butoxycarbonylaminomethyl]-benzoic acid ethyl ester. It is used further without purification.

(e) 7.1 g of the crude 4-[N-(2-isopropoxyethyl)-N-tert-butoxycarbonylaminomethyl]benzoic acid ethyl ester are dissolved in 70 ml of methylene chloride, and 40 ml of trifluoroacetic acid are added. The clear solution is left to stand overnight at room temperature and then concentrated by evaporation. The residue is taken up in methylene chloride, washed with aqueous ammonia solution (pH>9) and concentrated by evaporation. The oily/crystalline residue is dissolved in 50 ml of ethanol, and 50 ml of 2N sodium hydroxide solution are added. After stirring for 2 hours at 60°–65°, the solution is concentrated by evaporation and the residue is adjusted to pH 1 with water and 2N hydrochloric acid. The solution immediately becomes extremely cloudy and after about 5 minutes a precipitate forms. The mixture is concentrated by evaporation and the residue is heated briefly with 100 ml of ethanol. The solution is dried with magnesium sulfate, filtered over Hyflo and concentrated by evaporation. The crude crystalline material is suspended in 80 ml of tetrahydrofuran, and 3.2 g of chloroacetyl chloride are added. The suspension is stirred at room temperature for 14 hours, then concentrated to dryness by evaporation. The residue is dissolved in methylene chloride, washed with diluted hydrochloric acid, dried and concentrated by evaporation. Sticky, sparingly soluble crystals are obtained corresponding to 4-[N-(2-isopropoxyethyl)-N-chloroacetylaminomethyl]-benzoic acid.

(f) 2 g of the acid obtained under (e) are suspended in 35 ml of methylene chloride; 1.1 g of thionyl chloride and 2 drops of pyridine are added and the mixture is stirred overnight. The slightly cloudy solution is filtered over Hyflo and concentrated by evaporation, yielding the oily 4-[N-(2-isopropoxyethyl)-N-chloroacetylaminomethyl]-benzoic acid chloride.

EXAMPLE 2

1-{4-[2-(N-chloroacetylaminoethyl)]-benzoyl}-4-[2-(4-chlorophenyl)-ethyl]-piperazine hydrochloride 0.38 g of 1-[2-(4-chlorophenyl)-ethyl]-piperazine is dissolved with 0.22 g of Hünig base in 10 ml of methylene chloride. A solution of 0.44 g of crude 4-[2-(N-chloroacetylaminoethyl)]-benzoic acid chloride in approximately 10 ml of methylene chloride is added dropwise thereto. The clear solution so obtained is stirred overnight at room temperature. The methylene chloride solution is washed with water, dried over sodium sulfate and concentrated to dryness by evaporation. The crude oil (3.2 g) is chromatographed on silica gel (eluant: methylene chloride/methanol 250:10) and crystallised from ethanol and isopropanol in the form of the hydrochloride. The title compound having a melting point of 215°–216° is obtained.

The starting material is prepared as follows:

(a) 0.4 g of 4-[2-(N-chloroacetylaminoethyl)]-benzoic acid [Fujii et al., J. Pharm. Sci. 66 (1977) 844–848] is dissolved in 10 ml of tetrahydrofuran. 0.3 g of thionyl chloride and 2 drops of pyridine are added thereto. The suspension is stirred for 4 hours at room temperature, concentrated by evaporation and thoroughly dried. The crude 4-[(2-N-chloroacetylaminoethyl)]-benzoic acid chloride so obtained is used further without purification.

EXAMPLE 3

Tablets, each comprising 50 mg of 1-{4-[N-(2-isopropoxyethyl)-N-chloroacetylaminomethyl]-benzoyl}-4-[2-(4-chlorophenyl)-ethyl]-piperazine, or a salt thereof, for example the hydrochloride, are prepared as follows:

| Composition (10 000 tablets) | |
|---|---|
| active ingredient | 500.0 g |
| lactose | 500.0 g |
| potato starch | 352.0 g |
| gelatin | 8.0 g |
| talc | 60.0 g |
| magnesium stearate | 10.0 g |
| silicon dioxide (highly dispersed) | 20.0 g |

| Composition (10 000 tablets) | |
|---|---|
| ethanol | q.s. |

The active ingredient is mixed with the lactose and 292 g of potato starch, and the mixture is moistened with an ethanolic solution of the gelatin and granulated through a sieve. After drying, the remainder of the potato starch, the magnesium stearate, the talc and the silicon dioxide are mixed in and the mixture is compressed to form tablets each weighing 145.0 mg and comprising 50.0 mg of active ingredient; if desired the tablets may be provided with dividing notches for finer adaptation of the dose.

EXAMPLE 4

Hard gelatin capsules, each comprising 100 mg of active ingredient, for example 1-{4-[N-(2-isopropoxyethyl)-N-chloroacetylaminomethyl]-benzoyl}-4-[2-(4-chlorophenyl)-ethyl]-piperazine, or a salt thereof, for example the hydrochloride, are prepared as follows:

| Composition (for 1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added through a sieve of 0.2 mm mesh size to the lyophilised active ingredient. The two components are intimately mixed. Then first the lactose is added through a sieve of 0.6 mm mesh size and then the microcrystalline cellulose is added through a sieve of 0.9 mm mesh size. The mixture is then again intimately mixed for 10 minutes. Finally, the magnesium stearate is added through a sieve of 0.8 mm mesh size. After mixing for a further 3 minutes, 390 mg portions of the resulting formulation are introduced into size 0 hard gelatin capsules.

EXAMPLE 5

Film-coated tablets each comprising 100 mg of 1-{4-[N-(2-isopropoxyethyl)-N-chloroacetylaminomethyl]-benzoyl}-4-[2-(4-chlorophenyl)-ethyl]-piperazine, or a salt thereof, for example the hydrochloride, are prepared as follows:

| Composition (for 1000 film-coated tablets) | |
|---|---|
| active ingredient | 100.0 g |
| lactose | 100.0 g |
| corn starch | 70.0 g |
| talc | 8.5 g |
| calcium stearate | 1.5 g |
| hydroxypropylmethylcellulose | 2.36 g |
| shellac | 0.64 g |
| water | q.s. |
| methylene chloride | q.s. |

The active ingredient, the lactose and 40 g of the corn starch are mixed together and moistened with a paste prepared from 15 g of corn starch and water (with heating), and granulated. The granules are dried and the remainder of the corn starch, the talc and the calcium stearate are added and mixed with the granules. The mixture is compressed to form tablets (weight: 280 mg) which are then film-coated with a solution of the hydroxypropylmethylcellulose and the shellac in methylene chloride; final weight of the film-coated tablet: 283 mg.

EXAMPLE 6

A 0.2% injection or infusion solution of 1-{4-[N-(2-isopropoxyethyl)-N-chloroacetylaminomethyl]-benzoyl}-4-[2-(4-chlorophenyl)-ethyl]-piperazine, or a salt thereof, for example the hydrochloride, is prepared as follows:

| Composition (for 1000 ampoules) | |
|---|---|
| active ingredient | 5.0 g |
| sodium chloride | 22.5 g |
| phosphate buffer pH = 7.4 | 300.0 g |
| demineralised water | ad 2500.0 ml |

The active ingredient and the sodium chloride are dissolved in 1000 ml of water and filtered through a microfilter. The buffer solution is added and the mixture is made up to 2500 ml with water. For the preparation of unit dose forms, 1.0 ml or 2.5 ml portions are introduced into glass ampoules which then comprise 2.0 mg or 5.0 mg of active ingredient, respectively.

EXAMPLE 7

In a manner analogous to that described in Examples 3 to 6 it is also possible to prepare pharmaceutical compositions each comprising another of the compounds mentioned in Examples 1 and 2.

What is claimed is:

1. A compound of formula I

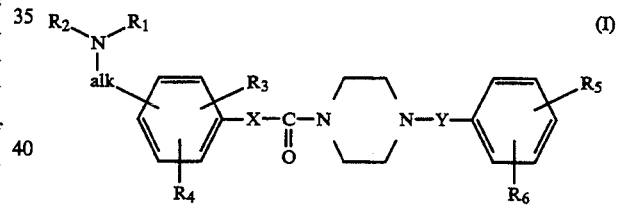

wherein
alk is lower alkylene;
(i) $R_1$ is
(a) hydrogen, lower alkyl, lower alkoxy-lower alkyl, or lower alkoxy-lower alkoxy-lower alkyl,
(b) phenoxy-lower alkyl or phenyl-lower alkoxy-lower alkyl, the phenyl group in each being unsubstituted or substituted by at least one substituent selected from lower alkyl, trifluoromethyl, lower alkoxy, halogen and hydroxy, or
(c) N-lower alkylamino-lower alkyl or N,N-dilower alkylamino-lower alkyl; and
$R_2$ is
(a) lower alkenoyl, (carboxy, lower alkoxycarbonyl, carbamoyl, N-lower alkyl-carbamoyl, N,N-dilower alkyl carbamoyl, or cyano)-lower alkenoyl, halo-lower alkanoyl, amino-lower alkanoyl, N-lower alkylamino-lower alkanoyl, N-[(carboxy or lower alkoxycarbonyl)-loweralkylamino]-lower alkanoyl, N,N-dilower alkylamino-lower alkanoyl, C4,6lower alkyleneamino-lower alkanoyl, morpholino-lower alkanoyl, thiomorpholino-lower alkanoyl, piperazino-lower alkanoyl (wherein the piperazino ring is unsubstituted or substituted in the 4-position by lower alkyl or by lower alkanoyl), hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, or lower alkylsulfonyl-lower alkanoyl, (b) phenylthio-lower alkanoyl, phenylsulfinyl-lower alkanoyl, or phenylsulfonyl-lower alkanoyl, the phenyl group in each of these three radicals being unsubstituted or substituted by at least one substituent selected from lower alkyl, lower alkoxy, halogen and hydroxy, or (c) carboxy-lower alkanoyl, lower alkoxycarbonyl-lower alkanoyl, carbamoyl-lower alkanoyl, N-lower alkylcarbamoyl-lower alkanoyl, N,N-diloweralkylcarbamoyl-lower alkanoyl, cyano-lower alkanoyl, carbamoyl, N-lower alkylcarbamoyl, N,N-dilower alkylcarbamoyl, carboxycarbonyl, lower alkoxycarbonyl-carbonyl, (carbamoyl, N-lower alkylcarbamoyl, or N,N-dilower alkylcarbamoyl)-carbonyl, lower alkanoyl, carboxy, lower alkoxycarbonyl, or phenyl-lower alkoxycarbonyl wherein the phenyl group is unsubstituted or substituted by at least one of lower alkyl, lower alkoxy, halogen, and hydroxy; or (ii) $R_1$ is lower alkoxy-lower alkyl and $R_2$ is hydrogen;

$R_3$ and $R_4$ are each independently of the other hydrogen, lower alkyl, halogen, lower alkoxy, or lower alkylthio;

$R_5$ and $R_6$ are each independently of the other hydrogen, lower alkyl, halo-lower alkyl, lower alkoxy, lower alkylthio, halogen, amino, lower alkylamino, dilower alkylamino, or alkanoylamino; and X and Y are each independently of the other a direct bond, lower alkylene, or lower alkenylene;

or a pharmaceutically acceptable salt thereof.

2. A compound of formula I according to claim 1, wherein alk is lower alkylene (i) $R_1$ is hydrogen, lower alkyl, lower alkoxy-lower alkyl, lower alkoxy-lower alkoxy-lower alkyl, phenoxy-lower alkyl, N-loweralkylamino-lower alkyl or N,N-dilower alkylamino-lower alkyl, and $R_2$ is lower alkenoyl, (carboxy or lower alkoxycarbonyl)-lower alkenoyl, halo-lower alkanoyl, N-lower alkylamino-lower alkanoyl, N-[carboxy or lower alkoxycarbonyl)-lower alkylamino]-lower alkanoyl, N,N-dilower alkylamino-lower alkanoyl, piperidino-lower alkanoyl, hydroxy-lower alkanoyl, lower alkoxy-lower alkanoyl, lower alkanoyloxy-lower alkanoyl, lower alkylthio-lower alkanoyl, lower alkylsulfinyl-lower alkanoyl, lower alkyl-sulfonyl-lower alkanoyl, phenylthio-lower alkanoyl, phenylsulfinyl-lower alkanoyl, phenysulfonyl-lower alkanoyl, carboxy-lower alkanoyl, lower alkoxycarbonyl-lower alkanoyl, or lower alkanoyl; or (ii) $R_1$ is lower alkoxy-lower alkyl and $R_2$ is hydrogen;

$R_3$ and $R_4$ are each independently of the other hydrogen, lower alkyl, halogen, lower alkoxy, or lower alkylthio;

$R_5$ and $R_6$ are each independently of the other hydrogen, lower alkyl, trifluoromethyl, lower alkoxy, lower alkylthio, halogen, or dilower alkylamino; and X and Y are each independently of the other a direct bond, lower alkylene, or lower alkylene;

or a pharmaceutically acceptable salt thereof.

3. A compound of formula I according to claim 1 wherein alk is methylene or 1,2-ethylene, $R_1$ is hydrogen, lower alkyl or lower alkoxy-lower alkyl, $R_2$ is lower alkenoyl, (carboxy or lower alkoxycarbonyl)-lower alkenoyl or halo-lower alkanoyl, or, when $R_1$ is lower alkoxy-lower alkyl, $R_2$ may also be hydrogen, $R_3$ and $R_4$ are each independently of the other hydrogen, lower alkyl, halogen, lower alkoxy or lower alkylthio, $R_5$ is lower alkylthio, chlorine, fluorine or bromine, $R_6$ is hydrogen, X is a direct bond or 1,2-ethenylene, and Y is 1,2-ethylene, or a pharmaceutically acceptable salt thereof.

4. A compound according to claim 1 of formula Ia

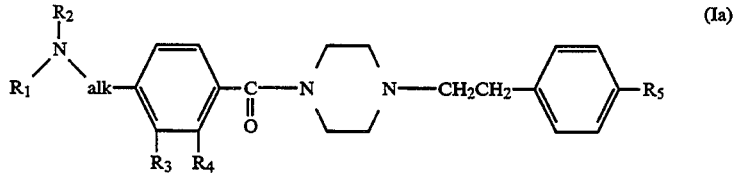

(Ia)

wherein alk is lower alkylene, $R_1$ is hydrogen, lower alkyl or lower alkoxy-lower alkyl, $R_2$ is lower alkenoyl, (carboxy or lower alkoxycarbonyl)-lower alkenoyl, or lower alkanoyl substituted by halogen, di-lower alkylamino, 4- to 6-membered lower alkyleneamino or by lower alkylthio, or, when $R_1$ is lower alkoxy-lower alkyl, $R_2$ may also be hydrogen, $R_3$ and $R_4$ are each independently of the other hydrogen, lower alkyl, chlorine, fluorine or bromine, and $R_5$ is lower alkylthio, chlorine, fluorine or bromine, or a pharmaceutically acceptable salt thereof.

5. A compound of formula Ia according to claim 4, wherein alk is $C_1$–$C_4$alkylene, $R_1$ is hydrogen, $C_1$–$C_4$alkyl or $C_1$–$C_4$alkoxy-$C_2$–$C_4$alkyl, $R_2$ is $C_3$–$C_7$alkenoyl, (carboxy or $C_1$–$C_4$alkoxycarbonyl)-$C_3$–$C_7$alkenoyl, chloro-$C_2$–$C_4$-alkanoyl, $C_1$–$C_4$alkylthio-, $C_1$–$C_4$alkylsulfinyl- or $C_1$–$C_4$alkylsulfonyl-$C_2$–$C_4$-alkanoyl, or, when $R_1$ is $C_1$–$C_4$alkoxy-$C_2$–$C_4$alkyl, $R_2$ may also be hydrogen, $R_3$ and $R_4$ are each independently of the other hydrogen, $C_1$–$C_4$alkyl, fluorine or chlorine, and $R_5$ is chlorine or bromine, or a pharmaceutically acceptable salt thereof.

6. A compound of formula Ia according to claim 4, wherein alk is methylene or 1,2-ethylene, $R_1$ is hydrogen, methyl, ethyl or 2-isopropoxyethyl, $R_2$ is prop-2-enoyl, 3-(carboxy or $C_1$-$C_4$alkoxycarbonyl)-prop-2-enoyl, chloroacetyl, 3-chloropropionyl, methylthioacetyl or ethylthioacetyl, $R_3$ and $R_4$ are each independently of the other hydrogen, methyl, fluorine or chlorine, and $R_5$ is chlorine or bromine, or a pharmaceutically acceptable salt thereof.

7. A compound of formula Ia according to claim 4, wherein alk is methylene or 1,2-ethylene, $R_1$ is hydrogen or 2-isopropoxyethyl, $R_2$ is chloroacetyl, $R_3$ and $R_4$ are each independently of the other hydrogen, methyl, fluorine or chlorine, and $R_5$ is chlorine or bromine, or a pharmaceutically acceptable salt thereof.

8. 1-{4-[N-(2-isopropoxyethyl)-N-chloroacetylaminomethyl]-benzoyl}-4-[2-(4-chlorophenyl)ethyl]-piperazine according to claim 1, or a pharmaceutically acceptable salt thereof.

9. 1-{4-[2-(N-chloroacetylaminoethyl)]-benzoyl}4-[2-(4-chlorophenyl)-ethyl]piperazine according to claim 1, or a pharmaceutically acceptable salt thereof.

10. A pharmaceutical composition for the treatment of diseases responsive to the inhibition of interleukin-1 comprising an interleukin-1 inhibiting effective amount of a compound according to claim 1 and a pharmaceutically acceptable carrier.

11. A method of treating a disease that is responsive to the inhibition of interleukin-1 in an animal in need thereof comprising administering to said animal an effective interleukin inhibiting amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 5,384,319
DATED : January 24, 1995
INVENTOR(S) : Ferrini

It is certified that error appears in the above-indentified patent and that said Letters Patent is hereby corrected as shown below:

Column 20, line 11, after "alkylene, or lower" delete "alkylene" and insert --alkenylene-- in liew thereof.

Signed and Sealed this

Fourth Day of April, 1995

*Attest:*

BRUCE LEHMAN

*Attesting Officer*  *Commissioner of Patents and Trademarks*